United States Patent [19]

Müller et al.

[11] Patent Number: 4,571,284

[45] Date of Patent: Feb. 18, 1986

[54] DEHYDRATING 2,6-DIMETHYLMORPHOLINE

[75] Inventors: Wolfgang H. E. Müller; Werner Böxkes, both of Marl; Heinz Scholten, Haltern, all of Fed. Rep. of Germany

[73] Assignee: Chemische Werke Hüls Aktiengesellschaft, Marl, Fed. Rep. of Germany

[21] Appl. No.: 673,405

[22] Filed: Nov. 20, 1984

[30] Foreign Application Priority Data

Nov. 22, 1983 [DE] Fed. Rep. of Germany ....... 3342009

[51] Int. Cl.$^4$ ...................... B01D 3/10; C07D 265/30
[52] U.S. Cl. ........................................ 203/14; 203/91; 544/106
[58] Field of Search ..................... 544/106; 203/14, 91

[56] References Cited

U.S. PATENT DOCUMENTS

| 2,129,805 | 9/1938 | Wilson | 544/106 |
| 2,717,232 | 9/1955 | Geller et al. | 203/14 |
| 3,083,202 | 3/1963 | Summers | 544/106 |
| 3,433,788 | 3/1969 | Somekh et al. | 203/61 |
| 4,212,972 | 7/1980 | Goetz et al. | 544/106 |
| 4,504,363 | 3/1985 | Goetz et al. | 203/14 |

FOREIGN PATENT DOCUMENTS

| 734935 | 5/1966 | Canada | 544/106 |
| 1263776 | 3/1968 | Fed. Rep. of Germany | 203/14 |

OTHER PUBLICATIONS

Lee H. Horsley: Azeotropic Data–III, Am. Chem. Soc., Wash. DC., 1973, pp. 626–628.

*Primary Examiner*—Wilbur Bascomb
*Attorney, Agent, or Firm*—Wells & Wells

[57] ABSTRACT

A separation of mixtures of water and 2,6-dimethylmorpholine is carried out by rectifying the mixtures at a pressure at the head of the column between 6 and 150 mbars. The separated 2,6-dimethylmorpholine has a maximum water content of 500 ppm by weight and it is possible to achieve for a corresponding design of the rectification water contents of less than 1 ppm by weight of dimethylmorpholine.

9 Claims, No Drawings

DEHYDRATING 2,6-DIMETHYLMORPHOLINE

CROSS-REFERENCE TO A RELATED APPLICATION

Applicants claim priority under 35 USC 119 for application P No. 33 42 009.2, filed Nov. 22, 1983, in West Germany.

BACKGROUND OF THE INVENTION

The field of the invention is the manufacture of 2,6-dimethylmorpholine and the invention is particularly concerned with dehydrating 2,6-dimethylmorpholine. The product obtained is practically dry when 2,6-dimethylmorpholine is isolated or recovered from aqueous solutions.

The state of the art of separating mixtures of water/2,6-dimethylmorpholine may be ascertained by reference to U.S. Pat. No. 3,083,202; J. Org. Chem., Vol. 11 (1946), pp. 286–291; and Chemical Abstracts, Vol. 40, 4732, 1–7, the disclosures of which are incorporated herein by reference.

U.S. Pat. No. 3,083,202 discloses the use of azeotropic rectification with an entrainer such as benzene for the separation of mixtures of water/2,6-dimethylmorpholine. Liquid-liquid extraction, using for instance ether for the dehydration of alkylmorpholine, is disclosed in the J. Organic Chem. and Chemical Abstracts articles incorporated above.

According to the state of the art, water and 2,6-dimethylmorpholine cannot be separated by simple rectification because they are fully miscible and form an azeotrope (70% by weight of water, b.p. 99.6° C.; Azeotropic data 111, System #567).

The entrainer rectification for drying liquids completely miscible with water is commercially available. However, it incurs the following drawbacks:

An additional column is required as a waste-water stripper because ecologically no water saturated with entrainer may be discharged into the environment. Introducing an accessory substance (entrainer) requires an additional supply storage with all the resulting drawbacks. Furthermore, there is the danger of contaminating the product with the accessory substance and also the problem of enriching by-products present in small amounts in the entrainer circuit, with the possibility of complications resulting from these enriched by-products. Again, there is the requirement to evaporate large amounts of entrainer and to condense them. Entrainer evaporation demands appreciable and additional energy.

SUMMARY OF THE INVENTION

Having in mind the limitations of the prior art there is a need for a simple, economical method for separating water and 2,6-dimethylmorpholine, which is free of the cited drawbacks.

Because practically all commercially available 2,6-dimethylmorpholine is water free or is used for further reactions or for separation into the cis-/trans isomers in water free form, the goal for the dehydrated product is a maximum water content of 500 ppm by weight in the 2,6-dimethylmorpholine following the separation of the two components. The separation of the components is applied to mixtures with arbitrary water contents.

According to the present invention, mixtures of water and 2,6-dimethylmorpholine are separated by rectification at a pressure between 6 and 150 mbars at the column head.

Preferably the pressure at the column head is 30 to 100 mbars.

DESCRIPTION OF THE PREFERRED EMBODIMENTS

The present approach gives new and unexpected results because it is known that substances will more easily form azeotropes when their boiling points are closer together as disclosed for instance by B. L. H. Horsley in "Azeotropic Data 111", p. 615, Washington, D.C. 1973. As regards the system water/2,6-dimethylmorpholine, the pressure data of the literature disclosed in West German Patent Application No. 2,938,698, and H. Booth, G. C. Gidley, "Tetrahedron", 21, (1965), pp 3429–34, shows that there is a larger spacing between the boiling points when the pressures are higher than when they are lower. Accordingly, any disappearance of azeotropy had to be expected at the higher rather than at the lower pressures. The present solution to the problem of dehydrating 2,6-dimethylmorpholine in no event could have been foreseen.

The process of the present invention can be carried out discontinuously or continuously.

The rectification of the present invention takes place when pressures at the column head are from 6 to 150 mbars, preferably at pressures from 30 to 100 mbars. Rectifying columns of conventional design are suitable, and columns with slight pressure losses per separation stage (less than or equal to 3.5 mbars/separation-stage) in the concentration part of the column are especially advantageous, while the pressure loss of the column discharge part assumes little significance. Accordingly, both tray columns and packed columns as well as columns having other special installations like Sulzer packages are useful.

The present process applies to all mixtures of water and 2,6-dimethylmorpholine, for instance to those which are obtained when 2,6-dimethylmorpholine is synthesized from bis-2-oxypropylamine by means of sulfuric acid. Following the separation of the sulfuric acid, they are in the form of sodium sulfate. No interference is experienced from small amounts of other materials forming azeotropically boiling mixtures with water and they can be separated together with the water, whereby purer 2,6-dimethylmorpholine is obtained than when other methods are used for dehydrating.

The process of the present invention offers a series of advantages over the methods known from the state of the art which employ accessory substances. Due to saving one column, capital costs are lower, the energy consumption is less, the purity of the product obtained is higher, and the by-products in the crude product interfere less. The water content of the 2,6-dimethylmorpholine rectified in conformity with the invention is at most 500 ppm by weight. Parts per million by weight values of less than 1 can be achieved by appropriate design of the rectification column and/or rectification conditions.

EXAMPLES

The examples below further illustrate the process and do not imply restriction in any way.

The series of examples shown in Table 1 indicates the effect of the pressure at the column head during rectification. All parameters except the head pressure are essentially kept appreciably constant.

This representation elucidates in definite manner the relation between the pressure at the head of the column and the reflux ratio. The lower the head pressure, the less the required reflux ratio. At a head pressure of 200 mbars, the reflux ratio is already so high that the process becomes uneconomical. At a pressure of 300 mbars, it is impossible any longer to achieve the desired separation. At a head pressure of less than 6 mbars, the separation no longer can be carried out because the reflux freezes. The boiling point at 6 mbars is about 0° C.

In the specific examples referred to in table 1 the column used is extended in the stripping section only by 10 plates in all cases, a sump product with a water content of less than the minimum detection limit of our method of analysis (10 ppm water by weight) was found.

In these examples the pressure difference was—depending on the number of plates—of course higher: 175 mbar.

TABLE 1

Examples of continuous rectification of mixtures of water and 2,6-dimethylmorpholine (column with 40 practical trays, of which 24 are in the concentrating part)

| Example No. | Pressure at head of column (mbar) | Pressure difference (mbar) | Required reflux ratio | % by weight water concentration in Intake | Distillate | Sump product |
|---|---|---|---|---|---|---|
| 1 | 10 | 140 | 0.8 | 75.0 | 99.96 | 0.010 |
| 2 | 30 | 140 | 1.0 | 75.0 | 99.80 | 0.005 |
| 3 | 50 | 140 | 1.1 | 75.0 | 99.88 | 0.008 |
| 4 | 75 | 140 | 1.4 | 75.0 | 99.91 | 0.012 |
| 5 | 100 | 140 | 1.7 | 75.0 | 99.88 | 0.003 |
| 6 | 150 | 140 | 2.6 | 75.0 | 99.75 | 0.009 |
| 7 | 200 | 140 | 4.1 | 75.0 | 99.89 | 0.005 |
| 8 | 300 | 140 | | 75.0 | (*) | 0.016 |

(*)Distillate concentrate of about 99.9% by weight of water could not be achieved.

It is well known to those skilled in the art that even though the number of trays of the rectifying column are varied, a specific reflux ratio nevertheless is kept, for instance three. Even then, just as in the present examples, the same concentration is almost always found at the column head and at the column bottom. However, this method does entail larger expenditure in cost of equipment without thereby achieving further insight. Another possibility is to keep the number of trays and the reflux ratio constant and to determine the dependency of the concentration obtained on the head pressure. Again, no further insight is offered by this approach. The object of the present invention is adequately disclosed by the parameters defined. One skilled in the pertinent field is capable to thereby apply this insight meaningfully to his particular separation problem.

Table 2 lists the results of three continuous (Examples 9-11) rectifications of industrial reaction products obtained in the synthesis of dimethylmorpholine, and besides cis- and trans-2,6-dimethylmorpholine and cis- and 2,5-dimethylmorpholine there also are present in small amounts a further series of partly unknown substances which split into distillate and sump products.

As shown by the analysis, these substances are preferentially separated in the procedure of the present invention together with the water from the 2,6-dimethylmorpholine to be produced, resulting in better product purity.

Example 11 shows that for a head column pressure greater than 150 mbars, there are relatively high contents of dimethylmorpholine in the head product (distillate, i.e., the separation no longer is satisfactory).

TABLE 2

Examples of continuous rectification of industrial mixtures

| Example # | 9 | 10 | 11 |
|---|---|---|---|
| Total number of trays | 40 | 40 | 40 |
| Trays in the reinforcing part | 30 | 30 | 30 |
| Reflux ratio | 1.33 | 1 | 1.33 |
| Pressure at column head (mbars) | 74 | 75 | 160 |
| Pressure at the column sump (mbars) | 130 | 125 | 212 |
| Temperature at column head (°C.) | 41 | 40 | 56 |
| Temperature at column sump (°C.) | 85 | 84 | 98 |
| Amount of distillate, referred to input (%) | 59.3 | 59.7 | 60.3 |
| Analysis (% by weight), input: water | 59 | 59.5 | 59 |
| 2,5- and 2,6-dimethylmorpholine | 40 | 39.55 | 40 |
| other substances | 1 | 0.95 | 1 |
| Analysis (% by weight), distillate: water | 99.3 | 99.1 | 97.7 |
| 2,5- and 2,6-dimethylmorpholine | 0.077 | 0.15 | 1.62 |
| other substances | 0.61 | 0.72 | 0.70 |
| Analysis (% by weight), sump product: water | 0.03 | 0.04 | 0.03 |
| 2,5- and 2,6-dimethylmorpholine | 98.44 | 98.60 | 98.95 |
| other substances | 1.49 | 1.31 | 1.02 |

What we claim is:

1. In the process for dehydrating 2,6-dimethylmorpholine by rectification the improvement comprising separating a mixture consisting essentially of water and said 2,6-dimethylmorpholine by rectification at a pressure between 6 and 150 mbars at the column head and recovering said 2,6-dimethylmorpholine having a water content less than 500 parts per million as a product from the sump.

2. The process of claim 1, wherein said pressure is between 30 and 100 mbars.

3. The process of claim 1, wherein a reflux ratio of 0.8 to 2.6 is maintained in the said rectification.

4. The process of claim 3, wherein said column has 40 practical trays.

5. The process of claim 4, wherein 24 of said trays are concentrating trays.

6. The process of claim 5, wherein a pressure difference of 140 mbars is maintained between said head and said sump.

7. The process of claim 1, wherein said column has 50 practical trays and said 2,6-dimethylmorpholine has a water content less than 10 parts per million.

8. The process of claim 7, wherein a pressure difference of 175 mbars is maintained between said head and said sump.

9. The process of claim 1, wherein a single column is used.

* * * * *